US008007815B1

(12) United States Patent
Granoff et al.

(10) Patent No.: US 8,007,815 B1
(45) Date of Patent: Aug. 30, 2011

(54) COMBINATION *MENINGITIDIS* B/C VACCINES

(75) Inventors: Dan M. Granoff, Berkeley, CA (US); Howard Raff, Mill Valley, CA (US); Ingeborg S. Aaberge, Oslo (NO); Bjorn Haneberg, Oslo (NO); Johan Holst, Oslo (NO)

(73) Assignees: Novartis AG, Basel (CH); Statens Institutt for Folkehelse, Oslo (NO)

( * ) Notice: Subject to any disclaimer, the term of this patent is extended or adjusted under 35 U.S.C. 154(b) by 0 days.

(21) Appl. No.: 09/701,453

(22) PCT Filed: May 28, 1999

(86) PCT No.: PCT/US99/11977
§ 371 (c)(1),
(2), (4) Date: Apr. 16, 2001

(87) PCT Pub. No.: WO99/61053
PCT Pub. Date: Dec. 2, 1999

Related U.S. Application Data

(60) Provisional application No. 60/087,351, filed on May 29, 1998, provisional application No. 60/106,446, filed on Oct. 30, 1998.

(51) Int. Cl.
*A61K 39/116* (2006.01)
*A61K 39/385* (2006.01)
*A61K 39/095* (2006.01)
*A61K 39/02* (2006.01)
*A61K 39/00* (2006.01)

(52) U.S. Cl. ............. 424/203.1; 424/197.11; 424/250.1; 424/184.1; 424/234.1; 424/236.1; 424/831; 424/832

(58) Field of Classification Search ............... 424/194.1, 424/197.11, 236.1, 237.1, 186.1, 193.1, 203.1, 424/234.1, 250.1, 831, 184.1; 536/123.1; 514/2, 23

See application file for complete search history.

(56) References Cited

U.S. PATENT DOCUMENTS

| | | | | |
|---|---|---|---|---|
| 4,707,543 A * | 11/1987 | Zollinger et al. | ............. | 530/402 |
| 5,846,735 A * | 12/1998 | Stapleton et al. | ............... | 435/7.1 |
| 6,180,111 B1 | 1/2001 | Stein et al. | | |
| 6,193,971 B1 * | 2/2001 | Hofmann et al. | .......... | 424/191.1 |
| 6,355,253 B1 | 3/2002 | Zlotnick | | |
| 6,413,520 B1 * | 7/2002 | Granoff | .................... | 424/197.11 |
| 6,451,317 B1 * | 9/2002 | Blake et al. | ............... | 424/197.11 |
| 6,476,201 B1 * | 11/2002 | Lowell et al. | .................. | 530/414 |
| 6,558,677 B2 * | 5/2003 | Zollinger et al. | .......... | 424/234.1 |
| 6,638,513 B2 * | 10/2003 | Seid | .......................... | 424/197.11 |
| 7,018,636 B1 | 3/2006 | Bhattacharjee et al. | | |
| 7,118,757 B1 * | 10/2006 | Seid et al. | .................. | 424/250.1 |
| 2006/0029621 A1 | 2/2006 | Granoff et al. | | |
| 2007/0082014 A1 | 4/2007 | Costantino | | |
| 2008/0241180 A1 | 10/2008 | Contorni | | |

FOREIGN PATENT DOCUMENTS

| | | |
|---|---|---|
| EP | 0011243 | 5/1980 |
| WO | WO 90/06696 | 6/1990 |
| WO | WO 98/58670 | * 12/1998 |
| WO | WO-99/33488 | 7/1999 |
| WO | WO-99/61053 | 12/1999 |
| WO | WO-01/34642 | 5/2001 |
| WO | WO-02/09643 | 2/2002 |
| WO | WO-2004/019977 | 3/2004 |
| WO | WO-2005/004908 | 1/2005 |

OTHER PUBLICATIONS

Costantino et al. Vaccine 10: 691-698, 1992.*
Granoff et al. Vaccine 11: S46-S51, 1993.*
van der Voort et al. Infect. immun. 64: 2745-2751, 1996.*
Paradiso et al. Dev. Biol. Stand. 87: 269-275, 1996.*
Corbel MJ. Biologicals 22: 353-360, 1994.*
Wetzler LM. Ann. N.Y. Acad. Sci. 730: 367-370, 1994.*
Glossary of Biochemistry and Molecular Biology. (Ed) Glick DM. Portland Press, London, p. 170, 1997.*
Dalseg et al. Vaccines 96. (Ed) F. Brown. Cold Spring Harbor Laboratory Press, Cold Spring Harbor, N.Y., pp. 177-182, 1996.*
Lowell et al. J. Exp. Med. 167: 658-663, 1988.*
Poolman et al. Antonie van Leeuwenhoek 53: 413-419, 1987.*
O'Hagan. J. Pharm. Pharmaco. 50: 1-10, Jan. 1998.*
Granoff et al. Infect. Immun. 65: 1710-1715, May 1997.*
Frasch CE. In: Development and Clinical Uses of Haemophilus B conjugate Vaccines. (Ed) Willis et al. M. Dekker, New York, pp. 435-453, 1994.*
Vella et al. Biotechnology 20: 1-22, 1992.*
Granoff et al. J. Pediatr. 121: 187-194, 1992.*
Fukasawa et al. FEMS Immunol. Med. Microbiol. 41: 205-210, Jul. 1, 2004.*
Lieberman et al., "Safety and Immunogenicity of a Serogroups A/C *Neisseria meningitidis* Oligosaccharide-Protein Conjugate Vaccine in Young Children" *JAMA* 275(19):1499-1503, May 15, 1996.
Milagres et al., "Antibody Studies in Mice of Outer Membrane Antigens for Use in an Improved Meningococcal B and C Vaccine" *FEMS Immunology and Medical Microbiology* 13:9-17, 1996.
Debbag et al., "Evaluation of Adverse Reactions Associated to Antimeningococcal BC Vaccination in 16.700 Children" *Clin. Infect. Dis.* vol. 21, Sep. 1995, p. 790-A420.
Granoff et al., "MF59 Adjuvant Enhances Antibody Responses of Infant Baboons Immunized with *Haemophilus influenzae* Type b and *Neisseria meningitidis* Group C Oligosaccharide-$CRM_{197}$ Conjugate Vaccine" *Infection and Immunity* 65(5):1710-1715, May 1997.
Rosenqvist et al., "Effect of Aluminium Hydroxide and Meningococcal Serogroup C Capsular Polysaccharide on the Immunogenicity and Reactogenicity of a Group B *Neisseria meningitidis* Outer Membrane Vesicle Vaccine" *Developments in Biological Standardization* 92:323-333, 1998.
Diaz Romero et al., "Current Status of Meningococcal Group B Vaccine Candidates: Capsular or non Capsular?" *Clinical Microbiology Reviews* 7(4), Oct. 1994.

(Continued)

*Primary Examiner* — S. Devi

(74) *Attorney, Agent, or Firm* — Amy Hessler; Otis Littlefield

(57) ABSTRACT

Combination vaccines for treating or preventing *Neisseria meningitidis* infection are described. The vaccines include *Neisseria meningitidis* serogroup B proteoliposomic vesicles and *Neissera meningitidis* serogroup C conjugated oligosaccharides.

11 Claims, 3 Drawing Sheets

OTHER PUBLICATIONS

Rappuoli, Rino, et al., (1996) "New Vaccines, Especially New Combined Vaccines," European Commission Cost/STD Initiative, Report of the Expert Panel VIII, Vaccine, 14: 691, 693-696.

"VA-MENGOC-BC," Producet information from S.C.S. Farmacia Manes, Argentina.

International Preliminary Examination Report mailed Aug. 23, 2000, for international patent application No. PCT/US99/11977, filed May 28, 1999.

Bjune et al. (1991). "Effect of outer membrane vesicle vaccine against group B meningococcal disease in Norway," Lancet 338(8775):1093-1096.

Fredriksen et al. (1991). "Production, characterization and control of MenB-vaccine "Folkehelsa": an outer membrane vesicle vaccine against group B meningococcal disease," NIPH Annals 14:67-79.

Katial et al. (2002). "Immunogenicity and Safety Testing of a Group B Intransal Meningococcal Native Outer Membrane Vesicle Vaccine," Infection and Immunity 70(2):702-707.

Koeberling et al. (2007). "Improved immunogenicity of a H44/76 group B outer membrane vesicle vaccine with over-expressed genome-derived Neisserial antigen 1870," Vaccine 25:1912-1920.

Peeters et al. (1996). "Phase I clinical trial with a hexavalent PorA containing meningococcal outer membrane vesicle vaccine," Vaccine 14(10):1009-1015.

\* cited by examiner

Ratios of Antibody Responses of Animals given Combination MenB OMV/MenC Conjugate with MF59 or Al(OH)$_3$

| ASSAY | | RATIO OF GMT MF59 : GMT Al(OH)$_3$ | |
| --- | --- | --- | --- |
| | | 28 DAYS POST-1 | 18 DAYS POST-2 |
| MenC | | | |
| | IgG | 1.6 | 6.0** |
| | BACTERICIDAL | 1.0* | 1.2* |
| MenB | | | |
| | IgG | 0.7 | 1.4 |
| | BACTERICIDAL | 0.9 | 1.4 |

*POOLED SERA ONLY TESTED          **P≤0.001

FIG. 3

Ratios of Antibody Responses of Animals given Combination/Al(OH)$_3$ vs. Monovalent/Al(OH)$_3$

| ASSAY | | RATIO OF GMT COMBO : GMT MONO | |
| --- | --- | --- | --- |
| | | 28 DAYS POST-1 | 18 DAYS POST-2 |
| MenC | | | |
| | IgG | 0.5 | 0.5 |
| | BACTERICIDAL | 0.2* | 0.7* |
| MenB | | | |
| | IgG | 1.3 | 1.2 |
| | BACTERICIDAL | 1.6 | 2.9** |

*POOLED SERA ONLY TESTED          **P≤0.05

FIG. 4

COMBINATION *MENINGITIDIS* B/C VACCINES

CROSS-REFERENCE TO RELATED APPLICATIONS

The present application claims priority to U.S. provisional application Ser. Nos. 60/087,351 filed May 29, 1998 and 60/106,446 filed Oct. 30, 1998, each of which is incorporated herein by reference in its entirety.

FIELD OF THE INVENTION

The present invention relates to combination immunogenic compositions and vaccines for *Neisseria meningitidis* B and C and to methods of inducing an immune response by administering the same.

BACKGROUND OF THE INVENTION

Serogroup B and C strains of *Neisseria meningitidis* (Nm) together account for the majority of invasive diseases in Europe and the United States. Vaccines against individual Nm serogroups are presently available. The NIPH (National Institute of Public Health of Norway) NmB vaccine is safe, elicits strain-specific immunity in children and adults, and is efficacious in preventing NmB disease in adolescents. This vaccine has been typically combined with meningococcal C polysaccharide vaccine and given with alum. The plain polysaccharide vaccine component, however, is not effective in infants and young children. The Chiron NmC conjugate (conj.) vaccine is also safe, elicits high titers of serum bactericidal antibody in infants vaccinated as young as two and three months of age, and induces immunologic B cell memory to the unconjugated NmC polysaccharide. Since both serogroups cause disease, a combination vaccine which induces an immune response to both serogroups would be highly advantageous.

SUMMARY OF THE INVENTION

In one aspect, the present invention relates to an immunogenic composition or vaccine comprising NmC oligosaccharides conjugated to a carrier protein, NmB outer membrane proteins, and a carrier. In a preferred embodiment, the carrier protein is $CRM_{197}$, a non-toxic diphtheria toxin, the NmB outer membrane proteins are presented as proteoliposomic vesicles, and the carrier is aluminum hydroxide or MF59.

In another aspect, the present invention relates to a method of inducing an immune response to NmB and NmC, or vaccinating, comprising the administration of an immunologically effective amount of an immunogenic composition comprising NmC oligosaccharides conjugated to a carrier protein, NmB outer membrane proteins, and a carrier.

BRIEF DESCRIPTION OF THE DRAWINGS

FIG. 3 summarizes the comparison of antibody ratios to NmB and NmC induced by the combination vaccine in MF59 adjuvant vs. Alum.

FIG. 4 summarizes the comparison of antibody ratios to NmB and NmC induced by the combination vaccine vs. the respective monovalent vaccine.

DETAILED DESCRIPTION OF PREFERRED EMBODIMENTS

Figure 1A:
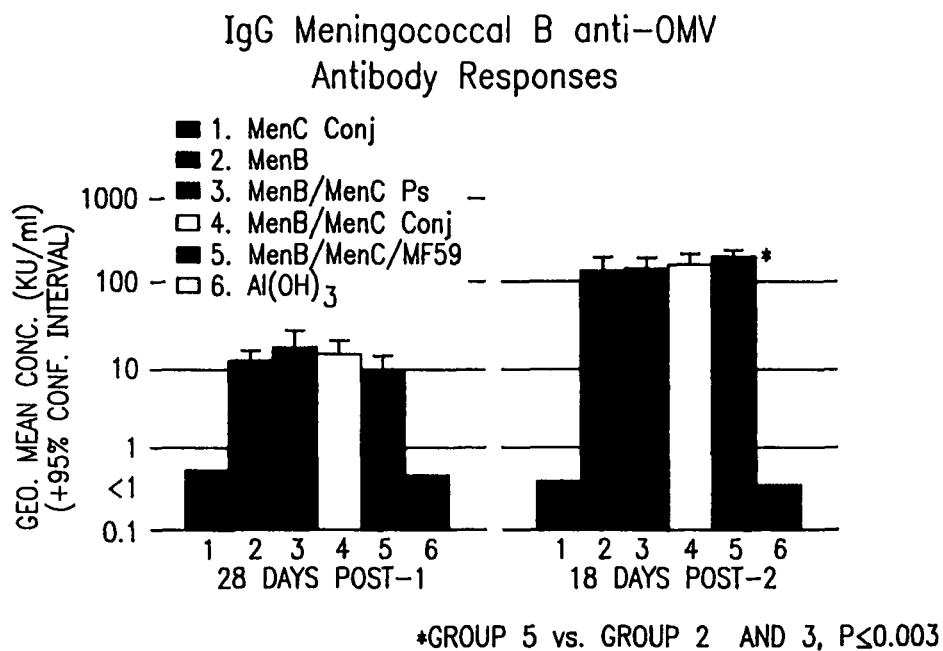
FIGS. 1A and 1B summarize NmB IgG and NmC IgG antibody titers, respectively, as determined by ELISA.

A combination vaccine for NmB and NmC which induces an immune response to both serogroups that is not significantly different from the immune response induced by each serogroup alone is described. The immunogenicity of the NIPH NmB vaccine (referred to herein as "NmB" or "MenB" vaccines) and the Chiron NmC conjugate vaccine (referred to herein as "NmC conj." or "MenC conj.), alone, in combination, and in combination with the adjuvant MF59 is described herein.

The practice of the present invention will employ, unless otherwise indicated, conventional methods of immunology and microbiology. Such techniques are explained fully in the literature. See, e.g., *Methods In Enzymology* (S. Colowick and N. Kaplan eds., Academic Press, Inc.) and *Handbook of Experimental Immunology*, Vols. I-IV (D. M. Weir and C. C. Blackwell eds., Blackwell Scientific Publications).

As used herein, the term "immunogenic" refers to material which induces the production of antibody upon administration to a vertebrate, including humans.

As used herein, the term "carrier" refers to a pharmaceutically acceptable component other than the NmB or NmC immunogenic component. The carrier can be organic, inorganic, or both. Suitable carriers well known to those of skill in the art and include, without limitation, large, slowly metabolized macromolecules such as proteins, polysaccharides, polylactic acids, polyglycolic acids, polymeric amino acids, amino acid copolymers, lipid aggregates (such as oil droplets or liposomes) and inactive virus particles. The carrier can also function as an immunostimulatory agent, e.g., adjuvant. Suitable adjuvants are well known to those of skill in the art.

As used herein, the term "immunologically effective amount," means the administration of that amount, either in a single dose or as part of a series, that is effective for inducing the production of antibody for either the treatment or prevention of disease. This amount will vary depending upon a variety of factors, including the physical condition of the subject, and can be readily determined by someone of skill in the art.

As used herein, the term "vaccine" means an immunogenic composition which is able to induce a microbicidal immune response. Preferably, the vaccines of the present invention elicit a bactericidal antibody response.

The present invention is directed, in part, to immunogenic compositions which induce an immune response to both *Meningitidis* B and C. In preferred embodiments of the invention, the immunogenic composition comprises NmB outer membrane protein, and NmC oligosaccharide conjugated to a first carrier.

The NmB protein preferably comprises partially purified outer membrane proteins from strain 44/76 (B15:P1.7, 16:L3, 7,9). The partially purified outer membrane proteins are preferably present as proteoliposomic vesicles as a result of the extraction process using deoxycholate. The dosage of NmB is expressed in µg of protein. Preferably, the NmB immune composition/vaccine components can be obtained from the National Institute of Public Health of Norway (NIPH). The NmB/alum vaccine comprises 0.05 mg/ml NmB protein, 3.33 mg/ml Al $(OH)_3$ (alum), and 0.10 mg/ml thiomersalsodium.

The Chiron oligosaccharide represents NmC polysaccharide fragments of from preferably about 12 to about 22 repeating units. Preferably, the NmC oligosaccharide is conjugated to a first carrier. The dosage of NmC conjugate or polysaccharide is expressed in µg of sialic acid. An NmC vaccine containing unconjugated polysaccharide (referred to herein as "NmC polysaccharide" or "MenC Ps") can also be used. MenC Ps is a crude isolate comprising polysaccharides preferably from about 60 to about 80 repeating units.

In preferred embodiments of the invention, the first carrier is a protein, polysaccharide, polylactic acid, polyglycolic acid, polymeric amino acids, amino acid copolymer, lipid aggregate, or inactive virus particle. More preferably, the first carrier is a protein. Most preferably, the first carrier is $CRM_{197}$. Ten µg of oligosaccharide to 12.5-33 µg $CRM_{197}$ (i.e., to maintain a oligo/protein ratio of from about 0.3 to about 0.8) is preferably used per dose. More preferably, about 20 µg of $CRM_{197}$ can be used.

In preferred embodiments of the invention, the immunogenic composition comprises a second carrier, preferably, aluminum hydroxide (alum) or MF59. Alum can be obtained from Superfos, Bedbaek, Denmark, and is a 3% solution. When present, about 1 mg to about 1.67 mg of alum is used per dose. MF59 is a micro-fluidized emulsion of squalene in water that has been shown to be safe and to augment serum antibody responses to a variety of investigational vaccines. MF59 comprises about 5% squalene, 0.5% TWEEN 80 and about 0.5% SPAN 85. The adjuvant MF59 is described in PCT publication No. WO 90/14837, incorporated herein by reference in its entirety. MF59 can be made according to the procedures described in, for example, Ott et al., *Vaccine Design: The Subunit And Adjuvant Approach*, 1995, M. F. Powell and M. J. Newman, Eds., Plenum Press, New York, p. 277-296; Singh et al., *Vaccine*, 1998 16, 1822-1827; Ott et al., *Vaccine*, 1995, 13, 1557-1562; and Valensi et al., *J. Immunol.*, 1994, 153, 4029-39, the disclosures of which are incorporated herein by reference in their entirety.

The immunogenic composition of the invention will employ an immunologically effective amount of the antigens. That is, there will be included an amount of antigen which, in combination with the adjuvant, will cause the subject to produce a specific and sufficient immunological response, preferably a T or B lymphocyte response, so as to impart protection to the subject from the subsequent exposure to *Neisseria*.

No single dose designation can be assigned which will provide specific guidance for each and every antigen which can be employed in this invention. The effective amount of antigen will be a function of its inherent activity and purity and is empirically determined by those of ordinary skill in the art via routine experimentation.

The immunogenic compositions according to the present invention comprise an immunostimulatory amount of *Neisseria* antigen. An immunostimulatory amount is that amount which is sufficient to induce a measurable humoral or cellular immune response. For example, the immunogenic compositions of the present invention comprise about 1 nanogram to about 1000 micrograms of antigen or about 10 nanograms to about 800 micrograms of antigen. In some preferred embodiments, the immunogenic compositions contain about 0.1 to about 500 micrograms of antigen. In some preferred embodiments, the immunogenic compositions contain about 1 to about 350 micrograms of antigen. In some preferred embodiments, the immunogenic compositions contain about 25 to about 250 micrograms of antigen. In some preferred embodiments, the immunogenic compositions contain about 100 micrograms of antigen. One skilled in the art can readily formulate an immunogenic composition comprising any desired amount of antigen, which can be empirically determined by those of ordinary skill in the art via routine experimentation. The immunogenic compositions can be conveniently administered in unit dosage form and can be prepared by any of the methods well known in the pharmaceutical art, for example, as described in Remington's Pharmaceutical Sciences (Mack Pub. Co., Easton, Pa., 1980), the disclosure of which is incorporated herein by reference in its entirety.

The present invention is also directed to vaccines comprising any of the immunogenic compositions described above.

The present invention is also directed to methods of inducing an immunologic response to NmB and NmC comprising administering an immunologically effective amount of an immunogenic composition described above to a human. Administration can be by any mode known to those skilled in the art including by oral, parenteral, pulmonary, transdermal, rectal, intraperitoneal, intramuscular, or subcutaneous routes.

The invention is further illustrated by way of the following examples which are intended to elucidate the invention. The foregoing examples are meant to illustrate the invention and are not to be construed to limit the invention in any way. Those skilled in the art will recognize modifications that are within the spirit and scope of the invention. All references cited herein are hereby incorporated by reference in their entirety.

EXAMPLES

Example 1

ELISA Results

Groups of guinea pigs (n=15 animals) were assigned to receive one of the following vaccines set forth in Table 1:

TABLE 1

| Group | Components | Amount per dose |
|---|---|---|
| Group 1 | NmC conj./alum | 10 µg/1 mg |
| Group 2 | NmB/alum | 25 µg/1 mg |
| Group 3 | NmC polysaccharide/NmB/alum | 10 µg/25 µg /1 mg |
| Group 4 | NmC conj./NmB/alum | 10 µg/25 µg/1 mg |
| Group 5 | NmC conj./NmB/MF59 | 10 µg/25 µg/0.5 ml. |
| Group 6 | (n = 5) comprised control animals that received alum alone. | |

Eighty guinea pigs were randomized into the groups set forth above and received one of six vaccine combinations. For the data presented in Table 2, each animal received two injections, IM, separated by 28 days. Serum samples were obtained prior to each injection, and 18 days after the second injection. For the data presented in FIGS. 1A and 1B, each animal received two immunizations separated by six weeks. Each dose consisted of two 0.25 ml IM injections. Serum samples were obtained immediately prior to each injection, and 14 or 18 days after the second injection.

Figure 1B:
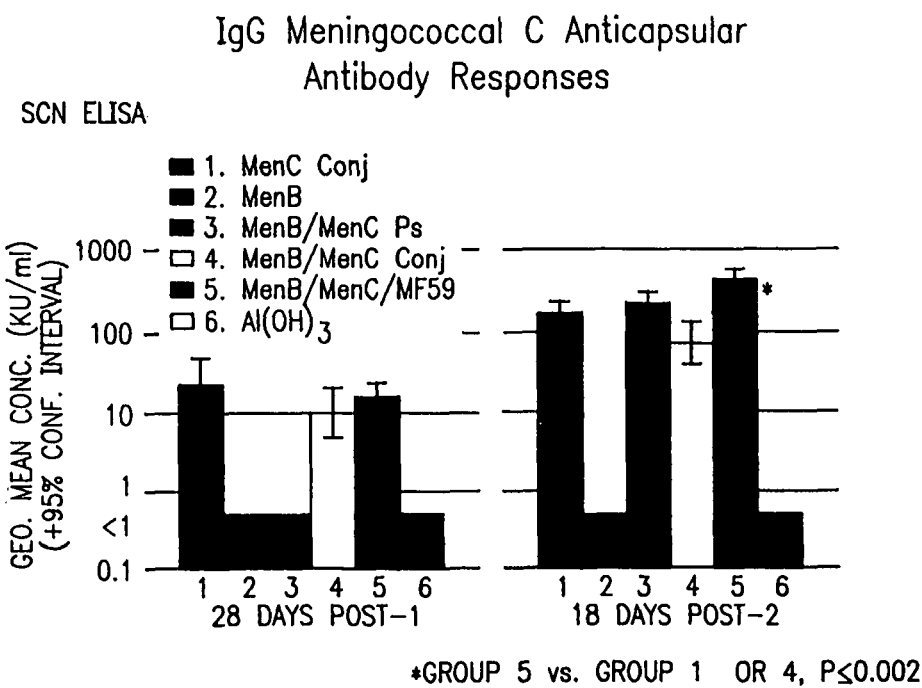

Serum samples were assayed for IgG anticapsular antibody concentrations to NmC (Table 2 and FIG. 1A) and for IgG anti-outer membrane vesicle antibody concentrations to NmB by ELISA (FIG. 1B). The ELISA data were generated in a representative assay of individual animal sera (Table 2) and also expressed as averages from a plurality of assays (FIGS. 1A and 1B). The summary ELISA data set forth in Table 2 are, therefore, expressed as geometric means.

For the ELISA, MCPS-ADH (NmC polysaccharide-adipic acid dihydrazide) conjugate or outer membrane vesicle (OMV) components was coated onto polystyrene microtiter plates overnight at 4° C., 1 µg/ml, 100 µl/well. On each coated plate, 100 µl/well of each of a reference standard (i.e., pooled guinea pig serum), a positive control, a negative control, and the serum samples were two-fold serially diluted in a buffer containing 75 µM ammonium thiocyanate, and incubated for two hours at room temperature. Rabbit anti-guinea pig IgG antibody conjugated to peroxidase was added to the wells (100 µl/well). After 2 hours, the colorimetric substrate 3,3',5, 5', Tetramethylbenzidine (TMB) (100 µl/well) was added, and the color was developed for 15 minutes. The levels of antibodies to MCPS ant to OMV present in the controls and samples were obtained from a standard curve using the reference standard which has an assigned value of 100 ELISA units/ml. The results are shown in Table 2 and FIGS. 1A and 1B.

The results summarized in Table 2 and FIGS. 1A and 1B reveal that the combination vaccine was immunogenic, as measured by NmB and NmC IgG antibody titers, respectively. FIG. 1A shows that a specific anti-meningococcal B antibody response was induced by the vaccine combinations comprising NmB. FIG. 1B shows that a specific antimeningococcal C antibody response was induced by the vaccine combinations comprising NmC. In particular, the antibody response induced by the combination of the NmC conjugate and NmB in the presence of MF59 adjuvant (Group 5) was significantly greater than the antibody response induced by either the NmC conjugate alone (Group 1) or the combination of the NmC conjugate and NmB in the presence of alum (Group 4). When the adjuvant MF59 was present, the antibody titer for the combination vaccine increased approximately six-fold.

TABLE 2

IgG MenC Antibody Responses (GMT)

| Vaccine | Adjuvant | SCN Assay Post-1 | Post-2 |
|---|---|---|---|
| MenC Conj. | Alum | 20.3 | 155 |
| MenB | Alum | <1 | <1 |
| MenC Ps + MenB | Alum | <1 | 1.5 |
| MenC Conj. + MenB | Alum | 9.5 | 71 |
| MenC Conj. + MenB | MF59 | 15.2 | 426 |
| none | Alum | <1 | <1 |

Example 2

Bactericidal Titers

Serum samples were tested for complement-mediated bactericidal titers to MenC strain 60E and MenB strain 44/76. Bactericidal titers were assayed on pooled sera from each group. Bactericidal data were generated using human complement.

Figure 2A:
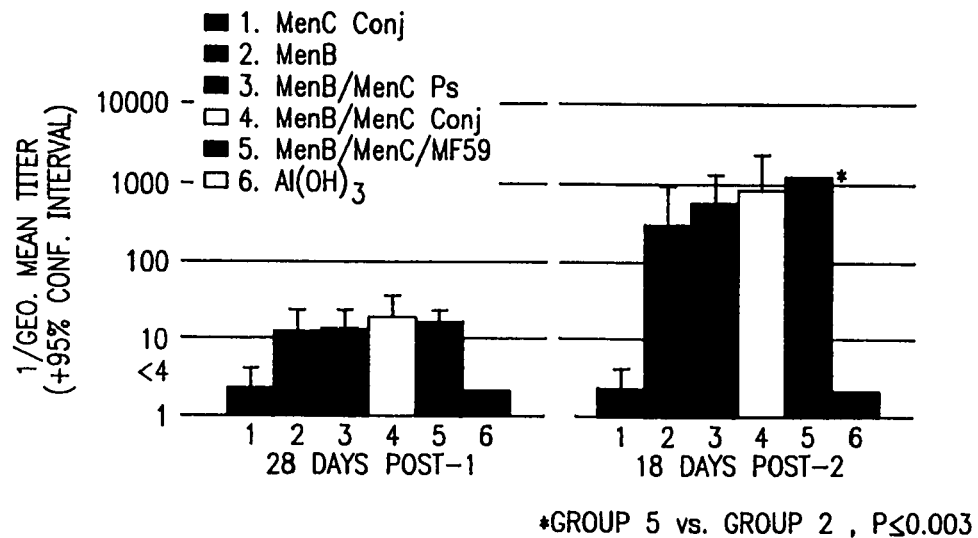
FIGS. 2A and 2B summarize of titers of serum bactericidal antibody to NmB and NmC, respectively.
Figure 2B:
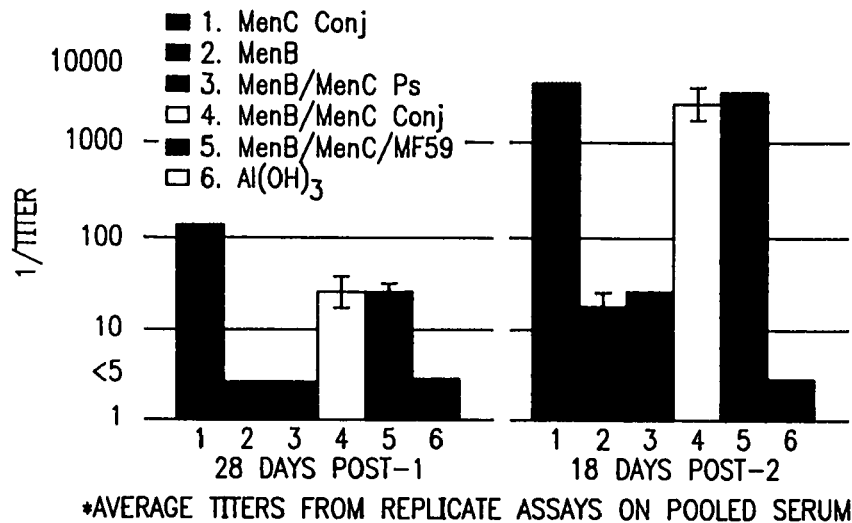

Components of the assay (i.e., buffer, antibody, complement, and bacteria) were added to sterile, 96-well tissue culture plates with lids (Nunc #167008). The plates were maintained at room temperature during the assay. To each well, 50 µGey's buffer (Gibco) containing 1% RIA Grade BSA (Sigma), 25 µl of the diluted test antibody, 25 µl of bacteria diluted 1:8000 in Gey's buffer/1% BSA, were sequentially added. Control wells include 1) Gey's buffer/1% BSA and bacteria alone (to determine if the organisms are viable in the diluent alone); 2) a time 0 control containing 75 µl buffer, 25 µl heat-inactivated (56° C., 30 min.) human complement, and 25 µl bacteria; and 3) a toxicity control testing the complement at 20% and 40% with buffer and bacteria to verify that the complement source is non-toxic to the test strain. All antibody samples (at the highest concentration assayed) were also tested with heat-inactivated complement to show that a decrease in colony forming units (cfu) in the presence of antibody is complement dependent. After all reagents were added, 22 µl was taken from each control well and plated onto Mueller-Hinton agar plates by allowing the sample to run from the top to the bottom of the plate, to determine the cfu in the well at 0 min. The microtiter plates were then covered and sealed with parafilm, and rotated gently for 1 hour at 37° C. in a 4% $CO_2$ incubator. The plates were then removed, and a 22 µl sample from each well plated on Mueller-Hinton agar. The culture plates were incubated for about 18 hours at 37° C., with 4% $CO_2$. The colonies were counted, and % survival determined for each test well: % survival=([cfu of sample well at 60 min]/[cfu in the heat inactivated complement control well at time 0 min.])×100. Bactericidal titers reported are those which resulted in 50% survival. Results from a single experiment are presented in Table 3. Results are also presented in FIGS. 2A and 2B, with FIG. 2B representing average titers from a plurality of experiments.

As the results summarized in Table 3 reveal, the combination vaccine elicited high titers of serum bactericidal antibody for both NmB and NmC. Bactericidal NmC antibody titer was slightly higher for the combination vaccine using MF59 as the carrier, but there was essentially no effect on bactericidal NmB titer using MF59. Interestingly, two- to five-fold higher NmB bactericidal titers were obtained with the combination vaccine than with the NmB vaccine alone. FIG. 2A demonstrates that the antibodies directed to meningococcal B induced by the vaccine combinations comprising NmB were bactericidal. FIG. 2B demonstrates that the antibodies directed to meningococcal C induced by the vaccine combinations comprising NmC conjugate were also bactericidal.

TABLE 3

| Group Vaccine | NmC (1/titer) Pre | Post-1 | Post-2 | NmB (1/titer) Pre | Post-1 | Post-2 |
|---|---|---|---|---|---|---|
| NmC conj. + Alum | <5 | 80 | >3375 | <5 | <5 | <5 |
| NmB + Alum | <5 | <5 | 15 | <5 | 15 | 800 |
| NmC Ps + NmB + Alum | <5 | <5 | 30 | <5 | 25 | 1500 |
| NmC Conj. + NmB + Alum | <5 | 25 | 2000 | <5 | 25 | 5000 |
| NmC Conj. + NmB + MF59 | <5 | 50 | >3375 | <5 | 25 | 4000 |
| Alum | <5 | <5 | <5 | <5 | <5 | <5 |

Example 3

Comparison of Alum and MF59 Adjuvants

Serum from the animals described above in FIGS. 1A and 1B were compared and MenC and MenB antibody responses generated by NmB/NmC conj. in either alum or MF59 adjuvant were detected as described above in Examples 1 and 2. The results, shown in FIG. 3, demonstrate that the antibody response to meningococcal C was approximately 6-fold greater in vaccines comprising MF59 adjuvant.

Example 4

Comparison of Antibody Responses Generated by Combination Vaccine to Monovalent Vaccines Serum from the animals described above in FIGS. 1A and 1B were compared and MenC and MenB antibody responses generated by NmB/NmC conj. were compared with the antibody responses generated by either the NmB vaccine alone or the NmC conj. alone in alum as described above in Examples 1 and 2. The results, shown in FIG. 4, demonstrate that there is no significant difference in the antibody responses to the components of the NmB/NmC conj. vaccine compared to the responses induced by the respective monovalent vaccines (either NmB or NmC conj.).

What is claimed is:

1. An immunogenic composition comprising a first antigen, a second antigen and an adjuvant, wherein: (a) the first antigen is a capsular oligosaccharide from serogroup C *N. meningitidis* (NmC) conjugated to $CRM_{197}$; (b) the second antigen is proteoliposomic vesicles from serogroup B of *N. meningitidis* (NmB); and (c) the adjuvant is MF59.

2. The composition of claim 1, wherein said NmC oligosaccharide contains 12 to about 22 repeating units from *N. meningitidis* serogroup C capsular polysaccharide.

3. The composition of claim 1, wherein said NmB is strain 44/76 (B15:P1.7, 16:L3,7,9).

4. The composition of claim 1, wherein said proteoliposomic vesicles are produced by a deoxycholate extraction process.

5. The composition of claim 1, wherein said carrier is polylactic acid or polyglycolic acid.

6. The composition of claim 1, wherein said composition comprises immunologically effective amounts of the first and the second antigen.

7. An immunogenic composition comprising an immunologically effective amount of a first antigen and an immunologically effective amount of a second antigen, wherein: (a) the first antigen is a capsular oligosaccharide from serogroup C *N. meningitidis* (NmC), conjugated to $CRM_{197}$, and contains from 12 to 22 repeating units from the NmC capsular polysaccharide and (b) the second antigen is proteoliposomic vesicles from strain 44/76 (B15:P1.7, 16:L3,7,9) of serogroup B *N. meningitidis* (NmB), wherein said proteoliposomic vesicles are produced by a deoxycholate extraction process.

8. The composition of claim 7, wherein said composition further comprises aluminum hydroxide or MF59.

9. The composition of claim 7, wherein said composition further comprises a carrier, wherein said carrier is polylactic acid or polyglycolic acid.

10. An immunogenic composition comprising a first antigen, a second antigen and an adjuvant, wherein: (a) the first antigen is a capsular oligosaccharide from serogroup C *N. meningitidis* containing 12 to about 22 repeating units from *N. meningitidis* serogroup C capsular polysaccharide conjugated to a carrier, and (b) the second antigen is proteoliposomic vesicles from serogroup B of *N. meningitidis* (NmB).

11. A method of inducing an immune response in a subject comprising administering an immunologically effective amount of the immunogenic composition of any one of claims 1, 2-4 and 5-9.

* * * * *